United States Patent
Wang et al.

(10) Patent No.: US 12,325,767 B2
(45) Date of Patent: Jun. 10, 2025

(54) DEGRADABLE MICROSPHERE AND USE THEREOF

(71) Applicant: Tsinghua University, Beijing (CN)

(72) Inventors: Jianbin Wang, Beijing (CN); Hongwei Wang, Beijing (CN); Junlong Yin, Beijing (CN); Meng Tian, Beijing (CN)

(73) Assignee: Tsinghua University, Beijing (CN)

( * ) Notice: Subject to any disclaimer, the term of this patent is extended or adjusted under 35 U.S.C. 154(b) by 1217 days.

(21) Appl. No.: 17/251,082

(22) PCT Filed: May 31, 2019

(86) PCT No.: PCT/CN2019/089508
§ 371 (c)(1),
(2) Date: Dec. 10, 2020

(87) PCT Pub. No.: WO2019/237952
PCT Pub. Date: Dec. 19, 2019

(65) Prior Publication Data
US 2021/0255074 A1    Aug. 19, 2021

(30) Foreign Application Priority Data
Jun. 13, 2018 (CN) .......................... 201810608246.5

(51) Int. Cl.
| | |
|---|---|
| C08F 220/56 | (2006.01) |
| B01D 15/38 | (2006.01) |
| B01D 21/26 | (2006.01) |
| C07K 1/14 | (2006.01) |
| C07K 1/22 | (2006.01) |
| C07K 1/36 | (2006.01) |
| C08J 3/075 | (2006.01) |
| G01N 1/40 | (2006.01) |
| G01N 21/64 | (2006.01) |
| G01N 23/04 | (2018.01) |
| G01N 23/06 | (2018.01) |
| G01N 33/68 | (2006.01) |
| H01J 49/00 | (2006.01) |

(52) U.S. Cl.
CPC ........ *C08F 220/56* (2013.01); *B01D 15/3809* (2013.01); *B01D 21/262* (2013.01); *C07K 1/145* (2013.01); *C07K 1/22* (2013.01); *C07K 1/36* (2013.01); *C08J 3/075* (2013.01); *G01N 1/4044* (2013.01); *G01N 1/405* (2013.01); *G01N 21/6458* (2013.01); *G01N 23/04* (2013.01); *G01N 23/06* (2013.01); *G01N 33/6848* (2013.01); *H01J 49/0031* (2013.01); *C08J 2333/26* (2013.01); *G01N 2223/04* (2013.01); *G01N 2223/418* (2013.01)

(58) Field of Classification Search
CPC .................................................. C08F 220/56
See application file for complete search history.

(56) References Cited

U.S. PATENT DOCUMENTS

| | | | | |
|---|---|---|---|---|
| 4,124,638 A | * | 11/1978 | Hansen | C08F 220/56 564/204 |
| 8,404,223 B2 | | 3/2013 | Garnett et al. | |
| 2010/0028445 A1 | | 2/2010 | Garnett et al. | |
| 2010/0143286 A1 | | 6/2010 | Matyjaszewski et al. | |
| 2014/0030350 A1 | * | 1/2014 | Ashrafi | A61K 31/197 424/501 |
| 2014/0037748 A1 | * | 2/2014 | Tang | A61K 38/162 424/490 |
| 2017/0260584 A1 | * | 9/2017 | Zheng | C12N 15/1065 |
| 2018/0334670 A1 | * | 11/2018 | Bharadwaj | C12N 15/1075 |

FOREIGN PATENT DOCUMENTS

| | | |
|---|---|---|
| CN | 101696272 | 4/2010 |
| CN | 103830752 | 6/2014 |
| CN | 105924373 | 9/2016 |
| JP | 2015184030 | 10/2015 |
| WO | WO 2005/013896 | 2/2005 |

OTHER PUBLICATIONS

KR-2015061111-A, Jun. 4, 2015, English abstract.*
EP Search Report in European Appln. No. 19819330.2, dated Feb. 15, 2020, 6 pages.
International Preliminary Report on Patentability in International Appln. No. PCT/CN2019/089508, dated Dec. 15, 2020, 9 pages (with English Translation).
International Search Report from WO 2019/237952 A1, dated Aug. 19, 2019, 2 pages.
CN Office Action in Chinese Appln. No. 201980039238.6, dated Mar. 18, 2022, 14 pages (with English Translation).

(Continued)

*Primary Examiner* — Margaret G Moore
(74) *Attorney, Agent, or Firm* — Fish & Richardson P.C.

(57) ABSTRACT

The present invention provides a degradable microbead comprising a polymer molecule crosslinked by a crosslinking agent, wherein the polymer molecule and/or the crosslinking agent comprises a sensitive chemical bond that is cleavable through a chemical and/or light treatment, thereby resulting in the degradation of the degradable microbead. The present invention also provides a method of separating a target protein from a sample. By using the degradation of the degradable microbead to replace an elution step in protein purification, it is possible to select a combination of target protein and affinity ligand with a stronger affinity, thereby improving the protein purification efficiency. The method is especially suitable for the high-throughput preparation of multiple protein samples, for example providing a protein sample for electron microscope observation or mass spectrometry measurement.

16 Claims, 6 Drawing Sheets

(56) References Cited

OTHER PUBLICATIONS

Feng et al., "Preparation of reduction-triggered degradable microcapsules for intracellular delivery of anti-cancer drug and gene," Polymer, 2014, 55:110-118.

Rapp et al., "Ruthenium-Crosslinked Hydrogels with Rapid, Visible-Light Degradation," Chem. Eur. J., 2018, 24:2328-2333.

* cited by examiner

DEGRADABLE MICROSPHERE AND USE THEREOF

CROSS-REFERENCE TO RELATED APPLICATIONS

This application is a U.S. national phase application under 35 U.S.C. § 371 of International Patent Application No. PCT/CN2019/089508, filed on May 31, 2019, which claims priority to Chinese Application No. 201810608246.5, filed on Jun. 13, 2018. The entire contents of the parent applications are hereby incorporated by reference.

TECHNICAL FIELD

The present invention relates to microbeads, especially microbeads degradable by a chemical or light treatment. The present invention also relates to uses of such microbeads in protein separation and electron microscope sample preparations.

BACKGROUND

A traditional protein preparation method generally includes the construction of expression plasmid, protein expression, and purification, so as to obtain the target protein having a relatively high purity. During this process, the purification step is relatively critical. It often requires a purification step by affinity chromatography to obtain a protein of high purity. This process mainly consists of three steps: loading onto column, washing, and eluting. Loading onto column is to adsorb the target protein on the chromatographic column. Washing is to wash the chromatographic column by a buffer solution not affecting the interaction between the target protein and the chromatographic column, to remove various impurities, including unbound target proteins. Eluting is to destroy the binding of the target protein to the corresponding antibody/ligand on the chromatographic column by a certain means (for example, using specific cleavages or competitive agents (such as enterokinase and biotin)), such that the target protein is eluted from the chromatographic column and dissolved in the solution.

In order that a target protein can be adsorbed by the chromatographic column materials, and also for the universality of the technical application, a general method is to add at the terminal of the target protein a specific tag (some short amino acid sequences), for example Flag tag and Strep tag, such that the obtained target protein can specifically bind to the corresponding antibody or ligand on the affinity chromatographic column (such as anti-Flag antibody and Streptactin protein), so as to achieve the capture of the target protein.

The traditional affinity chromatography suffers from the problem that in order to specifically capture a protein, the binding of the protein to its antibody/ligand must be strong enough so that nonspecifically bound molecules can be effectively washed; however, a too strong binding of the protein to the antibody/ligand is unfavorable to the protein elution. The contradiction between effective binding and effective elution often results in that during the affinity process a large amount of proteins are washed instead of being effectively bound to the chromatographic column, or a large amount of proteins are remained in the chromatographic column and cannot be eluted, leading to a usually much large loss of protein during the purification process. For example, it is typically needed to provide a large amount (e.g., 4-5 L) of cell or bacterial culture expressing the target protein, to obtain enough proteins for subsequent experiments.

On the other hand, in some applications, for example in studying the protein structure using electron microscopy, an amount of pure protein (at least 100 µg) is required. Therefore, if the above-mentioned purification method is used to prepare proteins for electron microscope observation, due to the problem of excessive loss during the purification process, it is necessary to provide enough samples to be purified (culture medium), which is obviously detrimental to the high-throughput preparation of protein samples. Currently, it is also a key point restricting the study on the protein structure by electron microscopy.

SUMMARY

To overcome the above problems, in one aspect, the present invention provides a degradable microbead comprising a polymer molecule crosslinked by a crosslinking agent, wherein the polymer molecule and/or the crosslinking agent comprises a sensitive chemical bond, wherein the sensitive chemical bond is cleavable through a chemical and/or light treatment, thereby resulting in the degradation of the degradable microbead.

In some embodiments, the sensitive chemical bond is provided by the a compound selected from the group consisting of cystamine-based compounds, o-nitrophenylethyl alcohol-based compounds or o-nitrobenzyl alcohol-based compounds, glycolide or lactide, and polypeptides having an internal proteolytic enzyme cleavage site.

Preferably, the polymer molecule is selected from the group consisting of polyacrylic acid-based compounds, polyacrylate-based compounds, polyacrylamide-based compounds, polyvinyl alcohol-based compounds, and polyethylene glycol-based compounds.

Preferably, the crosslinking agent is selected from the group consisting of cystamine-based compounds, o-nitrophenylethyl alcohol-based compounds or o-nitrobenzyl alcohol-based compounds, glycolide, lactide, and polypeptides having a proteolytic enzyme cleavage site.

More preferably, the crosslinking agent is cystamine bisacrylamide.

More preferably, the polymer molecule is a copolymer of acrylamide and cystamine acrylamide.

The degradable microbead of the present invention may be prepared by reacting in water-in-oil reaction droplets, wherein the aqueous phase may comprise acrylamide, cystamine bisacrylamide, cystamine acrylamide, and ammonium persulfate. In a specific embodiment, the aqueous phase comprises by weight 6% acrylamide, 0.2% cystamine bisacrylamide, 0.5% ammonium persulfate, and 75 mM cystamine acrylamide.

Preferably, the degradable microbead has a diameter of 1 µm to 100 µm.

In another aspect, the present invention also provides a method of separating a target protein from a sample, which comprises the steps of:
1) attaching an affinity ligand of the target protein to the degradable microbead;
2) contacting the sample with the degradable microbead, such that the target protein is attached to the degradable microbead by the affinity ligand;
3) separating the degradable microbead from the sample; and
4) degrading the degradable microbead by a chemical and/or light treatment to obtain the target protein.

In some embodiments, for example in case an active amino group is present on the polymer molecule, the step 1) of the method comprises attaching the affinity ligand to the degradable microbead by a coupling agent glutaraldehyde. In other embodiments, for example when an active aldehyde group is present on the polymer molecule, the affinity ligand may be directly attached to the active aldehyde group.

When the target protein is Flag-tagged, the affinity ligand may be an anti-Flag antibody; or when the target protein is Strep-tagged, the affinity ligand may be a Streptactin protein.

In some embodiments, the step 3) may be performed by chromatography or centrifugation.

In another aspect, the present invention also provides a method of observing a target protein by electron microscope, comprising separating the target protein by the above method, and observing the target protein by electron microscope.

In another aspect, the present invention also provides a method of analyzing a target protein by mass spectrometry, comprising separating the target protein by the above method, and analyzing the target protein by mass spectrometer.

In some embodiments, the analyzing comprises detecting the molecule weight, mutation, post-translational modification, or polymerization status of the target protein.

In some embodiments, the post-translational modification is acylation modification, alkylation modification, biotinylation modification, terpene-like modification, glycosylation modification, phosphorylation modification, esterification modification, nitrosation modification, ubiquitination modification, small ubiquitin-related modifier (SUMO) modification, amination modification, hydroxylation modification, or carboxylation modification.

In another aspect, the present invention also provides a method of qualitatively or quantitatively detecting a target protein in a sample, comprising a step of separating the target protein from the sample by the above method.

By using the degradation of the degradable microbead of the present invention to replace the common elution step in protein purification, it is possible to select a combination of target protein and affinity ligand with a stronger affinity, thereby improving the protein purification efficiency, which is especially suitable for the high-throughput preparation of multiple protein samples, for example providing protein samples for electron microscope observation or mass spectrometry measurement.

BRIEF DESCRIPTION OF THE DRAWINGS

FIG. 10A is a schematic diagram of the degradable microbead coupled with the protein on its surface. FIG. 10B shows the particle size distribution of the particles in the solution after the microbeads are degraded by DTT treatment. FIGS. 10C and 10D show the effects of DTT treatment time and treatment concentration on the microbead degradation, respectively.

FIG. 11E shows the results for the electron microscope observation of the 20S proteasome protein solution obtained through the traditional column purification treatment.

DESCRIPTION OF EMBODIMENTS

Unless specified otherwise, the technical and scientific terms used herein have the meanings commonly understood by one of ordinary skill in the art to which the present invention pertains.

The present invention provides a degradable microbead (hereinafter also referred to as "microbead" or "hydrogel microbead"), which is composed of polymer molecules and a crosslinking agent that crosslinks the polymer molecules together. The polymer molecule may be a "polyacrylamide-based molecule"; that is, in this polymer molecule, the acrylamide-based compound is used as the main polymerization monomer. The acrylamide-based compound may comprise, for example, acrylamide, N-hydroxymethylacrylamide, N-methylacrylamide, N-hydroxyethylacrylamide, and the like. The polymer molecule may also be polyacrylic acid-based, polyacrylate-based, polyvinyl alcohol-based, and polyethylene glycol-based molecules. The term "polyacrylic acid-based" means that the polymerization monomer of the polymer mainly comprises, for example, methacrylic acid, ethylacrylic acid, or mixtures thereof. Similarly, the terms "polyacrylate-based", "polyvinyl alcohol-based", and "polyethylene glycol-based" also have the meanings commonly understood by those skilled in the art.

In some embodiments of the present invention, the acrylamide is preferred, and the polyacrylamide molecule formed therefrom has the structure of Formula (I):

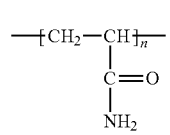
(I)

The crosslinking agent used is selected from the compounds which have the chemical bond therein cleaved under chemical treatments (comprising biological treatments, such as protease treatments) and/or light treatments (the cleavable chemical bond is also referred to herein as "sensitive chemical bond"). The compounds include, for example, cystamine-based compounds, o-nitrophenylethyl alcohol-based compounds or o-nitrobenzyl alcohol-based compounds. The cystamine-based compound can undergo an intramolecular disulfide bond cleavage in the presence of a reducing agent such as dithiothreitol (DTT) and 2-mercaptoethanol. As used herein, the term "and/or" includes any one of or a combination of the elements before and after this terms; for example, "chemical treatment and/or light treatment" refers to the chemical treatment, the light treatment, or the chemical and light treatments.

In some embodiments of the present invention, the cystamine bisacrylamide of the following formula may be used as the crosslinking agent:

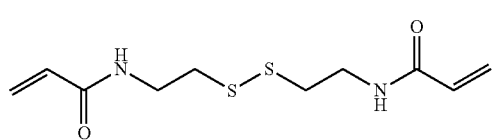
(II)

Figure 1:
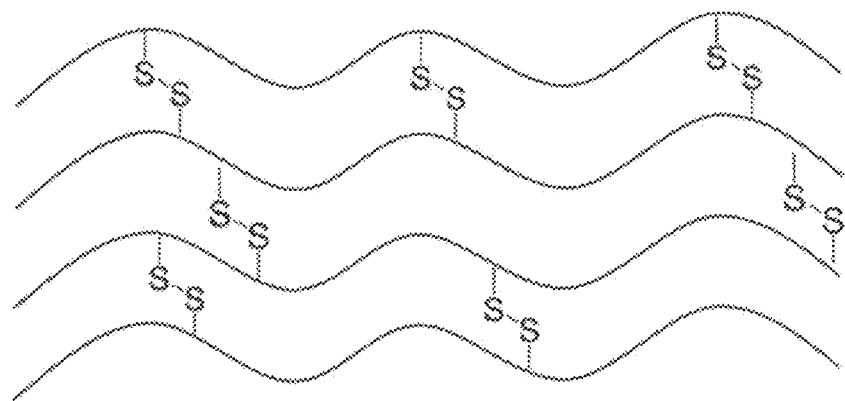
FIG. 1 is a schematic diagram of the structure of the degradable microbead using cystamine bisacrylamide as crosslinking agent according to the present invention. In the figure, the polymer molecules are represented by curves, and crosslinked with each other by a crosslinking agent having a disulfide bond.

The structure formed by crosslinking polyacrylamide molecules by cystamine bisacrylamide can be seen in FIG. 1.

A photosensitive crosslinking agent may include, for example, o-nitrophenylethyl alcohol-based compounds or o-nitrobenzyl alcohol-based compounds, p-hydroxyphenylacetoxy-based compounds, coumarin-based compounds, and the like. Due to the presence of o-nitro group, the o-nitrophenylethyl alcohol-based compound or o-nitrobenzyl alcohol-based compound forms a five-membered cyclic intermediate upon photo-excitation, thereby obtaining an o-nitrosoacetophenone-based compound, leading to the cleavage of intramolecular bond. In some embodiments of the present invention, for example, the o-nitrophenylethyl alcohol-based compound of formula (III) or (IV) may be used as the photosensitive crosslinking agent.

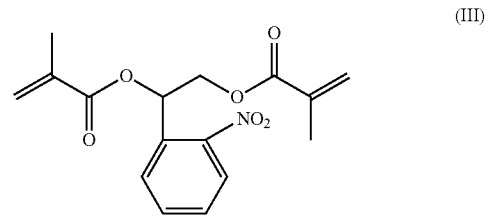
(III)

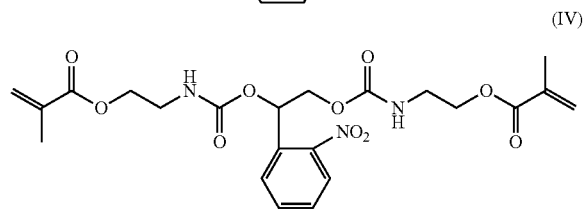
(IV)

It is also contemplated to use glycolide or lactide as the crosslinking agent, which can be hydrolyzed under heating in the presence of an acid or base.

In addition, it is also contemplated to use polypeptides containing a protease hydrolysis site as the crosslinking agent in the present invention, which are hydrolyzed in the presence of an appropriate protease.

Thus, the degradable microbead of the present invention may be subjected to the aforementioned chemical or light treatment, causing the intramolecular cleavage by the crosslinking agent, thereby leading to the degradation of the degradable microbead of the present invention.

Further, in order to facilitate the coupling of affinity ligand for protein purification to the degradable microbead (microbead surface and its internal cavity surface) of the present invention, the comonomer capable of providing an active group can be incorporated into the polymer molecule. For example, the active group is an amino group or aldehyde group. When the active group is amino group, the affinity ligand can be indirectly attached to the degradable microbead through a coupling agent such as glutaraldehyde. In a preferred embodiment, the comonomer is a cystamine acrylamide of formula (V) that can provide an active amino group:

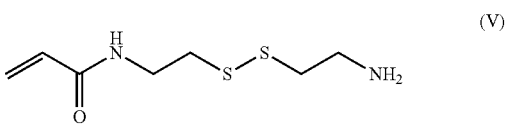
(V)

Figure 2:
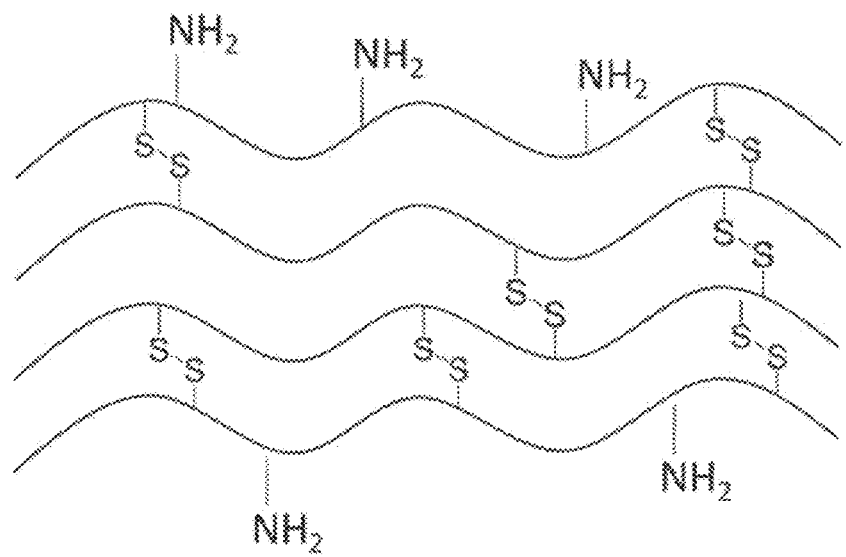
FIG. 2 is a schematic diagram of the structure of the degradable microbead with active amino groups according to the present invention.

The crosslinked polyacrylamide structure with active amino groups can be seen in FIG. 2.

Figure 3:
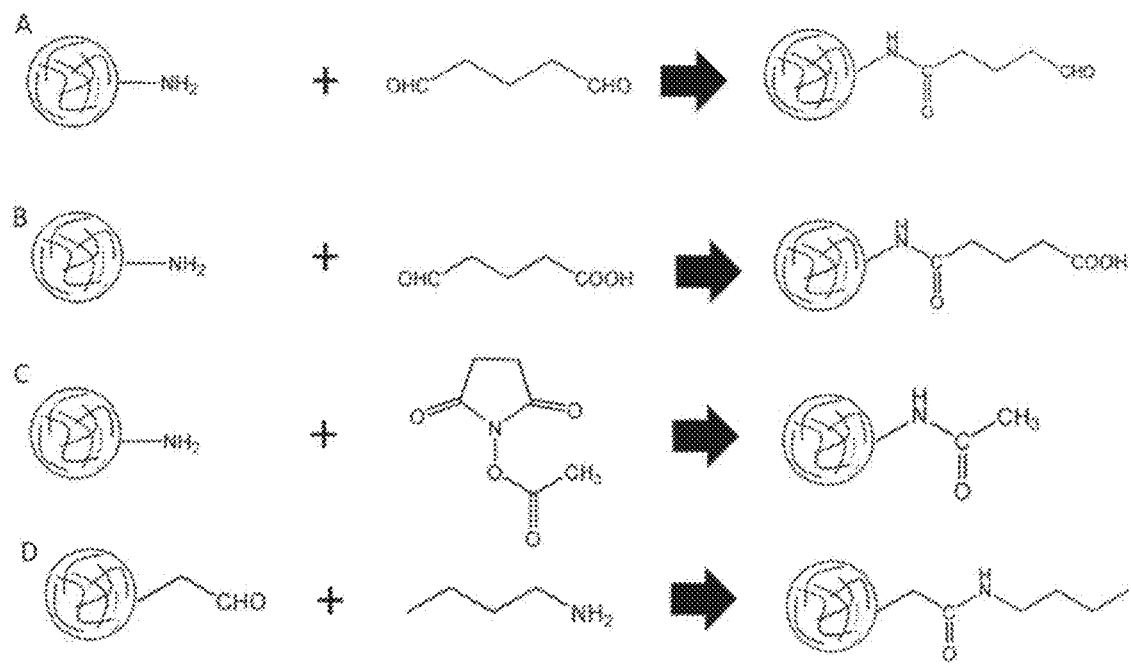
FIG. 3 shows exemplary reactions for various chemical modifications to the surface active groups of the degradable microbeads.

Upon the formation of the microbeads with active amino groups on the surface, the surfaces of the microbeads can be further processed or modified by various chemical means. FIG. 3 shows some exemplary chemical reactions. FIG. 3A shows that the hydrogel microbead with amino group modification is reacted with the coupling agent glutaraldehyde such that the surface of the hydrogel microbead is modified with the aldehyde group; FIG. 3B shows that the hydrogel microbead with amino group modification can be reacted with pivalic acid such that the surface of the hydrogel microbead is modified with the carboxy group; FIG. 3C shows that the hydrogel microbead with amino group modification is reacted with the amino group blocking agent N-succinimidyl acetate such that the amino group is inactivated; FIG. 3D shows that the hydrogel microbead with aldehyde group modification is reacted with the aldehyde group blocking agent with amino group such that the aldehyde group is inactivated.

When the crosslinking agent and the comonomer have the same sensitive bonds (such as disulfide bonds), on one hand the chemical or light treatment can cause the cleavage of the sensitive bond within the crosslinking agent, resulting in the degradation of the degradable microbead; meanwhile, it can also cause the cleavage of the sensitive bond within the comonomer, resulting in the separation of the target protein bound through the affinity ligand from the polymer molecule.

In some embodiments of the present invention, the sensitive bonds within the crosslinking agent and the comonomer are both provided by cystamine-based compounds, and are therefore sensitive to reducing agents such as DTT. In other embodiments of the present invention, the sensitive bonds within the crosslinking agent and the comonomer are both provided by o-nitrophenylethyl alcohol-based compounds or o-nitrobenzyl alcohol-based compounds, thereby being sensitive to light. In still other embodiments, the sensitive bonds within the crosslinking agent and the comonomer are provided by a cystamine-based mixture and a nitrophenylethanol-based compound or o-nitrobenzyl alcohol-based compound, respectively, thereby being sensitive to reducing agents and light, respectively.

The degradable microbeads of the present invention can be used to separate a target protein from a sample. In some cases, as described above, when preparing the degradable microbeads, the comonomers with active groups for coupling with affinity ligand can be incorporated into the polymer molecules. Alternatively, after the degradable microbeads are prepared, the active groups can be attached to the microbeads by chemical means so as to be coupled with affinity ligands. The term "affinity ligand" as used herein refers to any molecule capable of specifically binding to a target protein. Common protein binding means include antigen-antibody binding, ligand-receptor binding, and the binding of enzyme to its substrate. Accordingly, for example, the antibodies, ligands, and substrates can be coupled to degradable microbeads as affinity ligand, for the purpose of purifications and separations of corresponding proteins. In some embodiments, the target protein to be purified can also be expressed with a tag (short amino acid chain) for purification attached to its end, to form a fusion protein. In this case, an affinity ligand that specifically binds to this tag can be coupled to the degradable microbeads to separate the target protein from the sample. Commonly used tags include His tag (6 polyhistidine, specifically binding to metal ions such as $Ni^{2+}$), Flag tag (8 amino acid small peptide, binding to anti-Flag antibody), Strep tag (8 amino acid small peptide, specifically binding to Streptactin protein), and the like.

The degradable microbeads bound with affinity ligands can be poured into a chromatographic column as a filler to adsorb the target protein from the protein mixture liquid flowing through the chromatographic column and remove other impurities by washing; alternatively, the degradable microbeads can be directly added to the protein mixture liquid to be purified, and then the degradable microbeads having absorbed target proteins are separated from other ingredients by centrifugation. Finally, the sensitive covalent bonds within the crosslinking agents in the degradable microbeads are broken by a chemical and/or light treatment and the microbeads are degraded. The obtained target proteins at this time could be directly used in various biochemical tests, such as Western-blotting (Western Immunoblotting) and electron microscope observation. Since the degradation of the microbeads is used to replace protein elution, a combination of target protein and affinity ligand with a closer binding can be selected, thus improving the efficiency of protein purification, without worry about elution efficiency.

Based on actual testing, for Western-blotting, the binding of a target protein to its affinity ligand will cause a gel shift, but it will not affect the detection of the target protein (for both qualitative and quantitative determination). For electron microscope observation, the binding of a target protein to its ligand will reduce the possibility of protein orientation to some extent, and it is easier to obtain a fine structure of the protein in a certain orientation. Thus, the protein separation method provided by the present invention is suitable for high-throughput protein purification, for example providing protein samples for electron microscope observation.

Figure 4:
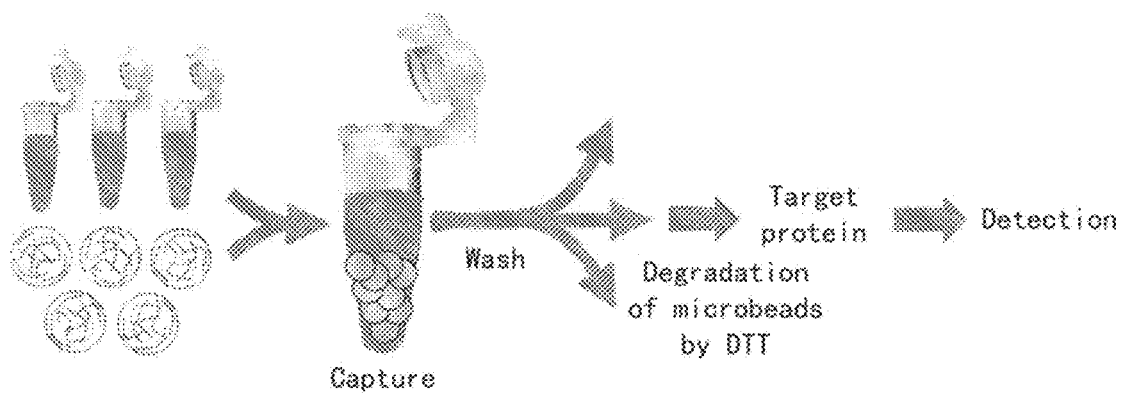
FIG. 4 is an exemplary flow chart of using the degradable microbead of the present invention in the protein separation.

FIG. 4 shows an exemplary flow chart of using the degradable microbeads of the present invention in the preparation of electron microscope samples. The mixture containing the target protein to be purified is mixed with the degradable microbeads with the corresponding affinity ligand according to the present invention. After the microbeads bind to the target protein, they are washed and degraded by DTT to obtain the samples used for electron microscope observation.

In addition, it can be expected that the microbeads of the present invention can be used for nucleic acid molecule purification besides protein purification and separation. For example, a short nucleotide chain can be coupled to the microbeads to separate from a mixture of nucleic acid molecules the target nucleic acid molecule that can hybridize with the short nucleotide chain.

The following Examples further illustrate the present invention.

Figure 5:
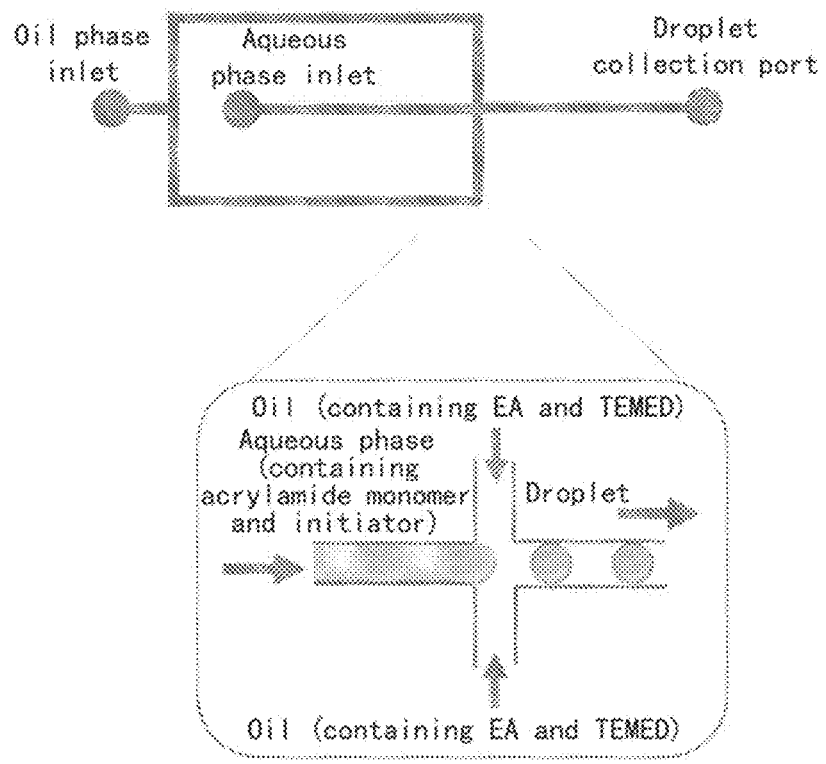
FIG. 5 is a schematic diagram of preparing a degradable microbead using a cross-shaped channel microfluidic chip.

Example 1 Preparation of Hydrogel Microbeads with Active Groups 1.1 Reagents
HFE-7500 (3M Novec, Novec 7500)
EA (RAN Biotechnologies, 008-FluoroSurfactant-2wtH-50G)
Acrylamide (Sigma, A9099-25G)
Cystamine bisacrylamide (Sigma, A4929-5G)
Cystamine acrylamide (self-made)
APS (ammonium persulfate, Sigma, A3678-25G)
TEMED (tetramethylethylenediamine, Sigma, T9281-25ML)
PFO (1H,1H,2H,2H-Perfluorooctanol, perfluorooctanol, Sigma, 370533-25G)
Microbead washing buffer: 10 mM Tris-HCl pH 8.0; 0.1 mM EDTA; 0.1% (v/v) Tween 1.2 Preparation Process First, the acrylamide polymerization reaction droplets wrapped in the oil phase were formed by using the cross-shaped channel microfluidic chip as shown in FIG. 5. The three holes from left to right in the upper panel are the oil phase input port, the aqueous phase input port, and the droplet collection port. The lower panel illustrates in details various liquid flows and droplet formation process at the center of the cross. The oil phase contained 1% (w/w) EA and 0.8% (v/v) TEMED in HFE-7500; and the aqueous phase contained 6% acrylamide, 0.2% cystamine bisacrylamide, 75 mM cystamine acrylamide, and 0.5% APS in water. The flow rate of the oil phase was controlled to 1500 μl/h, and the flow rate of the aqueous phase was controlled to 800 μl/h. The acrylamide polymerization reaction droplets generated by the cross-shaped channel microfluidic chip was passed into 500 μl of mineral oil, and left at room temperature for 8 hours to complete the polymerization reaction.

Upon completion of the polymerization reaction of reaction droplets, the upper mineral oil was removed by the pipette. Then 500 μl of microbead washing buffer and 100 μl of PFO were added, and mixed thoroughly by shaking. After centrifugation at 1,000 g for 1 min, the upper aqueous phase was removed. Then 500 μl of microbead washing buffer was added, and mixed gently by pipetting. After the lower oil phase was settled down, the upper turbid liquid containing microbeads was transferred to a new tube. Subsequently, the microbeads were washed twice with the microbead washing buffer, and for each time, the upper liquid was removed by centrifugation at 1,000 g for 1 min, and the resultant spherical particles were recovered to obtain the hydrogel microbeads with amino group modification.

Figure 6:
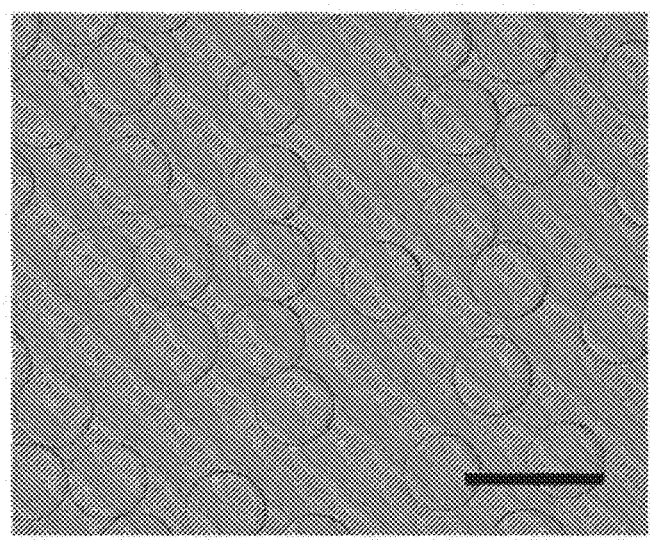
FIG. 6 is an electron microscope image of the degradable microbead prepared in the present invention.
Figure 7:
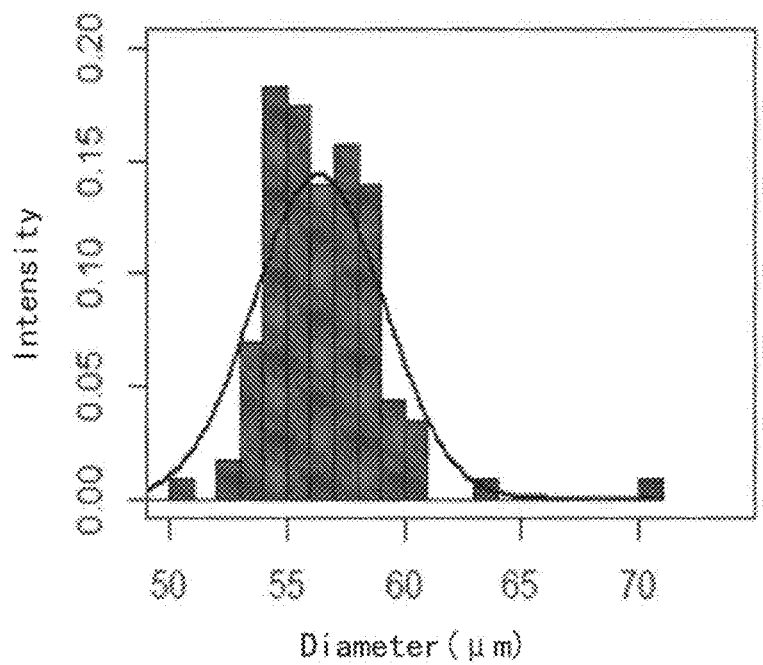
FIG. 7 is a histogram showing the diameter distribution of the degradable microbead prepared in the present invention.

FIG. 6 shows the bright-field microscope image of the prepared microbeads, with a magnification of 40, and a scale of 100 μm in the figure. The statistical histogram for the microbead diameter is shown in FIG. 7, wherein the horizontal axis represents the microbead diameter in micrometer (μm), and the longitudinal axis represents the microbead count. The mean diameter was 56 μm, the standard deviation was 2.77, and the coefficient of variation (CV) was 5%. The hydrogel microbeads itself or having absorbed proteins can be degraded in a DTT environment (see Example 4 below).

Example 2 Modification of Surface Groups on Hydrogel Microbeads 2.1 Reagents
Glutaraldehyde solution (Sigma, G7651-10ML)
Glycine (Sigma, 50046-50G)
DTT (dithiothreitol, Sigma, 43815-1G)
Tween 20 (Sigma, P7949-100ML)
Tris-HCl pH 8.0 (amresco, E199-100ML)
NaCl (Invitrogen, AM9760G)
EDTA (amresco, E522-100ML)
NaCNBH3 (Sigma, 156159)
N-Succinimidyl acetate (J&K, 142162)
EDC (1-(3-dimethylaminopropyl)-3-ethyl carbodiimide hydrochloride, Sigma, E1769-1G)
Microbead washing buffer: 10 mM Tris; 0.1 mM EDTA; 0.1% (v/v) Tween 20
Strep tag protein buffer: 20 mM Tris; 0.04% Tween 20; 50 mM NaCl; 1 mM EDTA 2.2 Reaction Process The hydrogel microbeads obtained in Example 1 was exemplified. Through a series of chemical reactions, the surfaces of the hydrogel microbeads can be modified with aldehyde groups, carboxyl groups, or other active groups, and certain active groups may also be blocked. The aldehyde group modification was exemplified by the following process: the surface of the microbeads was modified with the aldehyde group via the reaction of glutaraldehyde with the amino group on the surface of the microbeads. The remaining amino groups were then blocked through a chemical reaction to obtain the hydrogel microbeads with aldehyde group modification. The aldehyde group can be reacted with a suitable reactant such as the affinity ligand described above, followed by blocking the remaining aldehyde groups by a chemical reaction.

2.2.1 Aldehyde Group Modification

The reaction mixture was formulated in accordance with Table 1 below by using the microbeads prepared in Example 1. The reaction mixture was mixed gently, and placed on a shaker at 4° C. overnight for evenly mixing. Thereafter, the microbeads were washed twice with the microbead washing buffer, and for each time, the upper solution was removed by centrifugation at 1,000 g for 1 min, and the microbeads modified by aldehyde groups were recovered.

TABLE 1

Composition of the reaction mixture for aldehyde group modification

| Reagent | Final concentration |
| --- | --- |
| Microbeads prepared in Example 1 | 10000 |
| Glutaraldehyde | 250 mM |
| NaCNBH3 | 20 mM |
| Microbead washing buffer | |
| Total | 50 μl |

2.2.2 Amino Group Blocking

The reaction mixture was formulated in accordance with Table 2 below by using the microbeads modified by aldehyde groups as obtained in step 2.2.1. The reaction mixture was mixed gently, and placed on a shaker at 4° C. for 4 hours for mixing evenly. Thereafter, the microbeads were washed twice with the microbead washing buffer, and for each time, the upper solution was removed by centrifugation at 1,000 g for 1 min, then the microbeads were recovered.

TABLE 2

Composition of reaction mixture for amino group blocking

| Reagent | Final concentration |
| --- | --- |
| Microbeads obtained in step 2.2.1 | 10000 |
| N-Succinimidyl acetate | 50 mM |
| EDC | 20 mg/ml |
| Microbead washing buffer | |
| Total | 50 μl |

2.2.3 Aldehyde Group Blocking

The reaction mixture was formulated in accordance with Table 3 below by using the microbeads obtained in step 2.2.2. The reaction mixture was mixed gently, and placed on a shaker at 4° C. for 4 hours for mixing evenly. Thereafter, the microbeads were washed twice with the microbead washing buffer, and for each time, the upper solution was removed by centrifugation at 1,000 g for 1 min, then the microbeads were recovered.

TABLE 3

Composition of the reaction mixture
for aldehyde group blocking

| Reagent | Final concentration |
|---|---|
| Microbeads obtained in step 2.2.2 | 10000 |
| Glycine | 1.5M |
| NaCNBH3 | 20 mM |
| Microbead washing buffer | |
| Total | 50 μl |

In practical applications, generally after the affinity ligand for binding to a target protein is coupled to the microbeads by using aldehyde groups, the remaining aldehyde groups on the microbeads are blocked by this step.

Example 3 Use of Hydrogel Microbeads in Protein Purification

In order to enable the specific binding of the hydrogel microbeads to a target protein, it is needed to couple a specific affinity ligand to the hydrogel microbeads. This Example illustrates the use of the hydrogel microbeads of the present invention in green fluorescent protein (GFP) enrichment. For the enrichment of GFP, an anti-GFP antibody (anti-GFP antibody, Abcam, ab13970) was selected to be coupled to the hydrogel microbeads. The surface of the microbeads was selected to be modified with the aldehyde group so as to react with the amino group of anti-GFP antibody, to achieve the purpose of coupling the antibody to the hydrogel microbeads. In order that the already prepared hydrogel microbeads with amino groups on the surface were modified with a sufficient number of aldehyde groups, the glutaraldehyde was selected as the coupling agent.

3.1 Preparation of the Hydrogel Microbeads with Amino Group on the Surface as Well as Aldehyde Group Modification and Amino Group Blocking After the hydrogel microbeads with amino groups have been prepared (see the preparation method in Example 1), the surfaces of the hydrogel microbeads were modified with aldehyde groups as described in Example 2, and then the amino groups not involved in the reaction were blocked to reduce the subsequent side reactions.

3.2 Affinity Ligand Coupling and Aldehyde Group Blocking

The reaction mixture was then formulated in accordance with Table 4 below. The reaction mixture was gently mixed, and placed on a shaker at 4° C. overnight for mixing evenly. Thereafter, the microbeads were washed twice with the microbead washing buffer, and for each time, the upper solution was removed by centrifugation at 1,000 g for 1 min, then the microbeads were recovered.

TABLE 4

Composition of the reaction mixture
for coupling with anti-GFP antibody

| Reagent | Final concentration |
|---|---|
| Microbeads obtained in step 2.2.2 of Example 2 | 10000 |
| Anti-GFP antibody | 0.5 mg/ml |
| NaCNBH3 | 20 mM |
| Microbead washing buffer | |
| Total | 50 μl |

Then, according to the reaction system described in 2.2.3 of Example 2, the aldehyde groups not involved in the coupling of the anti-GFP antibody were blocked, to obtain hydrogel microbeads coupled with anti-GFP antibodies on the surfaces.

3.3 the Capture and Fluorescence Detection of Target Protein

Figure 8:
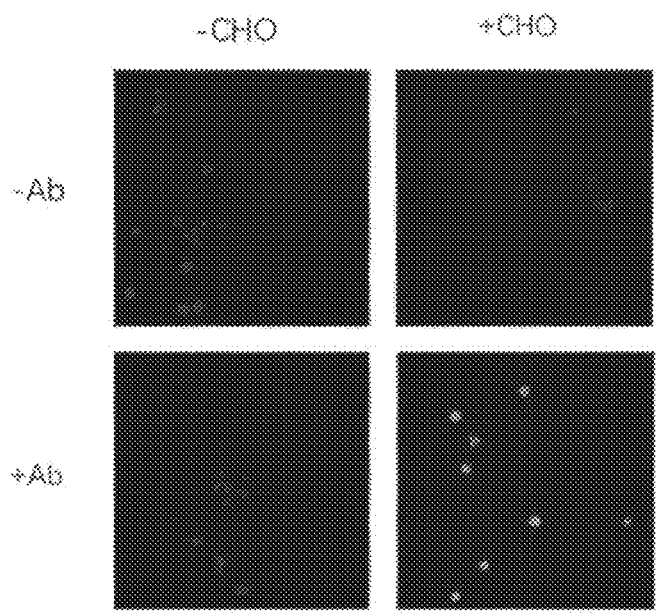
FIG. 8 is a fluorescence microscope image showing the binding of the degradable microbead coupled with anti-GFP antibody of the present invention to GFP, as compared with the degradable microbead without aldehyde group modification and/or without being coupled with anti-GFP antibody.

The hydrogel microbeads were mixed with a cell lysate overexpressing GFP, and left at 4° C. overnight. The microbeads were then washed twice with the microbead washing buffer, and for each time, the upper solution was removed by centrifugation. The fluorescence of the microbeads was observed under the fluorescence microscope. The results are shown in FIG. 8. Compared with the control microbeads not modified by aldehyde group (–CHO) or not coupled with anti-GFP antibody (–Ab), the polyacrylamide microbeads coupled with anti-GFP antibody could effectively capture GFP, and thus green color can be observed under the fluorescence microscope, while green color cannot be observed for the control microbeads under the fluorescence microscope. In the figure, –CHO represents that the microbeads are not modified with aldehyde groups, and +CHO represents that the microbeads are modified with aldehyde groups. +Ab represents that the microbeads are coupled with anti-GFP antibodies, and –Ab represents that microbeads are not coupled with anti-GFP antibodies.

Figure 9:
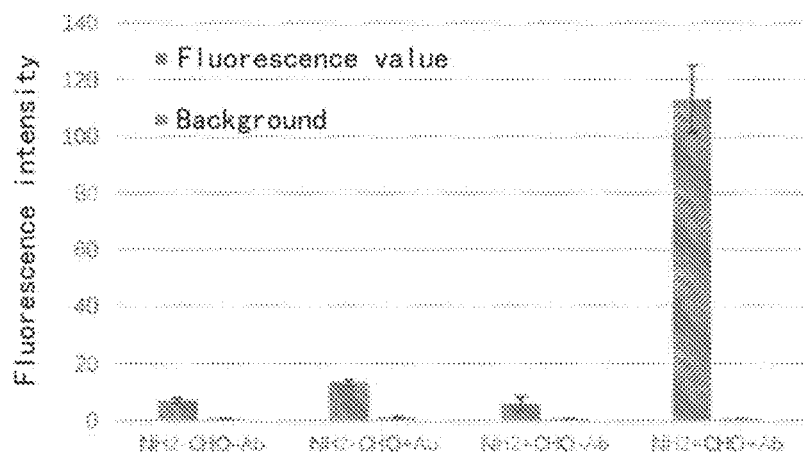
FIG. 9 is a bar graph showing the fluorescence intensity of the binding of the degradable microbead coupled with anti-GFP antibody of the present invention to GFP, as compared with the degradable microbead without aldehyde group modification and/or without being coupled with anti-GFP antibody.

Subsequently, confocal fluorescence microscope (Zeiss, LSM780) was used to quantify the GFP intensity. The fluorescence intensity of the control group was close to the background noise, while a stronger fluorescence signal could be detected for the group coupled with anti-GFP antibody. The fluorescence intensities of the hydrogel microbeads obtained through the statistics by software (Zeiss, ZEN_2011_Lite_x64) are shown in FIG. 9 (n=5). In the figure, NH2-CHO-Ab represents that the prepared microbeads with amino groups on the surfaces are not subjected to aldehyde group modification and antibody coupling treatment; NH2-CHO+Ab represents that the prepared microbeads with amino groups on the surfaces are subjected to the coupling treatment of step 3.2 without aldehyde group modification; NH2+CHO-Ab represents that the prepared microbeads with amino groups on the surfaces are subjected to the aldehyde group modification without antibody coupling treatment; and NH2+CHO+Ab represents that the prepared microbeads with amino groups on the surfaces are subjected to aldehyde group modification and antibody coupling treatment.

3.4 Degradation of Microbeads and Detection of GFP Protein Content

The GFP-bound hydrogel microbeads were degraded and then the GFP content was detected by Western blotting assay. The detailed operations were as follows: DTT was added to the degradable microbeads obtained in step 3.3 with a final concentration of 5 mM. The mixture was gently mixed by hand, and placed on a shaker at 4° C. for 0.5 h for mixing evenly, then centrifuged with a horizontal rotor at 1,000 g for 1 min, and the lower insoluble substances were discarded. The upper solution contained the purified target protein GFP, which can be used for the subsequent Western-blotting assay. For Western blotting, the binding of the target protein to its affinity ligand can cause a gel shift, but it will not affect the detection of the target protein content and the like.

Example 4 Solubility Test for Hydrogel Microbeads 4.1 Reagents
DTT (dithiothreitol, Sigma, 43816-10ML)

4.2 Experiment Operations and Results

Figure 10:
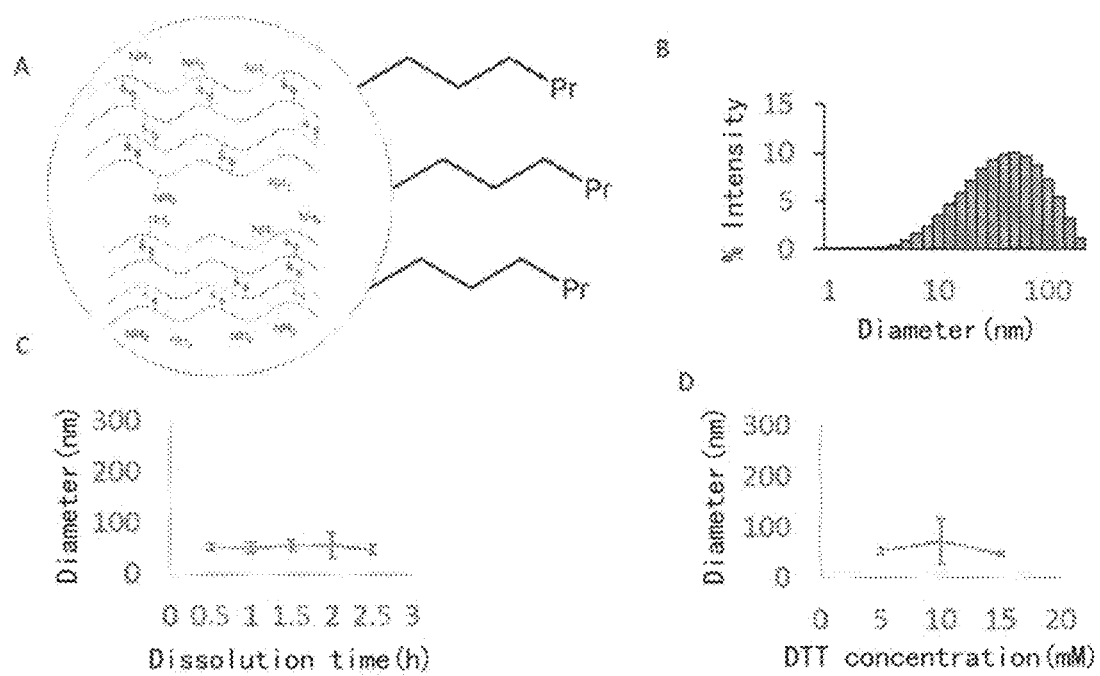
FIG. 10 shows the dissolution characteristics of the degradable microbead coupled with an affinity ligand (protein) in the present invention.

The solubility test for hydrogel microbeads is performed in this Example. The microbeads prepared in step 3.2 of Example 3 were dissolved in a 5 mM DTT solution for 30 min. Upon detection, the microbeads were dissolved to form smaller nano-scale particles (see FIG. 10). FIG. 10A is a schematic diagram of the microbeads coupled with anti-GFP antibody. Using dynamic elastic scattering, the particle size distribution of particles in the solution after the dissolution of the microbeads was obtained. FIG. 10B shows a histogram of particle size distribution, in which an approximately normal distribution is presented. μ=57.62 nm, σ=6.706, CV=11.64%. The DTT concentration or dissolution time used was also changed to make the dissolved nano-scale particles more uniform. From the results of dynamic elastic light scattering, the dissolution of microbeads could only reach the order of hundreds nanometers. It is expected that by making the diameters of the dissolved small particles more uniform, the influences on the various subsequent experiments and electron microscope observations will be reduced. Later experiments also proved that these small particles did not affect the observation of the transmission electron microscope. FIG. 10C shows the change of particle size over time under the treatment at a concentration of 5 mM, and FIG. 10D shows the change of particle size over DTT concentration for the same treatment time (30 min). From these figures, it can be seen that dissolving with 5 mM DTT for 30 min leads to an almost complete dissolution of microbeads with an original particle size of about 60 microns, and the average diameter of the nano-scale particles after the dissolution is about 57 nanometers. Through testing, it is confirmed when the ratio of the number of DTT molecules to that of beads reached $10^{12}$:1, the microbeads could be effectively degraded.

Example 5 Enrichment of 20S Proteasome by Hydrogel Microbeads 5.1 Reagents
Streptactin (Bio-rad, 1610381)
20S proteasome (20S proteasome, self-made)

5.2 Experiment Process and Results

Streptactin was coupled based on the microbeads prepared in Example 1 by a method similar to that described in Example 2 and Example 3, to capture Strep-tagged 20S proteasomes from the lysates of the protein-expressing cell culture.

Figure 11:
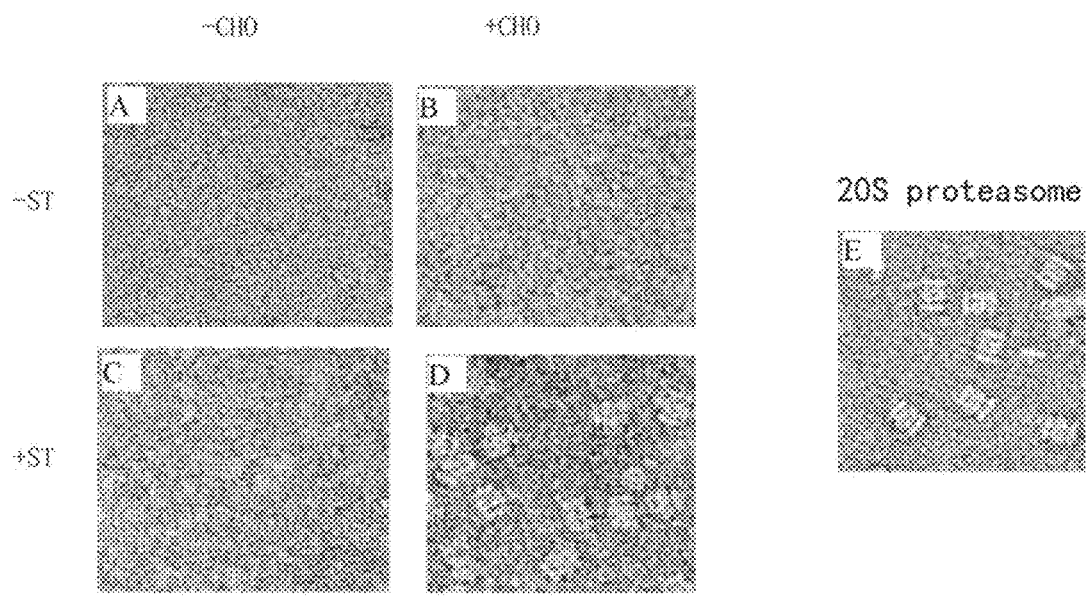
FIG. 11 shows a series of electron microscope images for verifying that the degradable microbead of the present invention can effectively capture the target protein which is then used for electron microscope observation after the degradation of the microbead. The degradable microbead coupled with Streptactin according to the present invention captures the target protein from the cell culture lysate expressing the target protein (Strep-tagged 20S proteasome), then the microbead is treated by DTT, and the obtained protein sample is suitable for electron microscope observation (FIG. 11D). The degradable microbead without aldehyde group modification and/or without being coupled with anti-GFP antibody cannot capture the target protein from the lysate (FIGS. 11A to C).

After being coupled with Streptactin, the hydrogel microbeads were mixed in the solution of strep-tagged 20S proteasome overnight. After washing the microbeads thrice, the microbeads were degraded by DTT. The electron microscope sample was prepared by negative staining, and the protein purity and status were characterized by electron microscope. The results of the transmission electron microscope at room temperature are shown in FIG. 11. The Strep-tagged 20S proteasomes can be effectively separated by the microbeads coupled with Streptactin, and the protein status can meet the requirements of electron microscope observation. The degraded microbeads do not affect the electron microscope observation. FIG. 11A is an electron microscope image of the microbeads without aldehyde group modification and in the absence of Streptactin; FIG. 11B is an electron microscope image of the microbeads with aldehyde group modification and in the absence of Streptactin; FIG. 11C is an electron microscope image of the microbeads without aldehyde group modification and in the presence of Streptactin (the coupling step similar to Example 3 was performed, but the microbeads were not previously modified by aldehyde groups); and FIG. 11D is an electron microscope image of the microbeads with aldehyde group modification and Streptactin coupling. The results show that the microbeads without aldehyde group modification or in the absence of Streptactin cannot effectively adsorb the target protein 20S proteasome. FIG. 11C shows a slight difference between FIG. 11A and FIG. 11B, presumably because Streptactin is non-specifically adsorbed on the microbeads, but the adsorption level is significantly different from that of FIG. 11D. FIG. 11E shows the results observed under the electron microscope for the 20S proteasome solution obtained through the traditional column purification treatment after preparing the electron microscope sample by negative staining. The electron microscope results in FIG. 11D and FIG. 11E are consistent, indicating that it is simple and feasible to prepare the protein sample for electron microscope by the degradable microbeads of the present invention.

It should be understood by those skilled in the art to which the present invention pertains that the methods and materials described above are merely exemplary, and should not be construed to limit the scope of the present invention.

Example 6 Enrichment of Avidin Protein by Hydrogel Microbeads 6.1 Reagents
NHS-Biotin (AAT Bioquest, 3010)
Avidin-1 (Sigma, A8706, corn recombinant source)
Avidin-2 (Sigma, A9275, egg white source)

6.2 Experiment Process and Results

Biotin was coupled based on the microbeads prepared in Example 1 by the reaction between amino group and NHS, to capture avidin-1 from E. coli lysate containing avidin-1 (avidin at a concentration of 10 μg/100 μL, and E. coli protein at a concentration of 200 μg/100 μL).

After being coupled with Biotin, the hydrogel microbeads were mixed in above E. coli lysate containing avidin-1 overnight. After the microbeads were washed thrice by the above microbead washing buffer, the buffer was replaced with 20 mM ammonium acetate solution, and the microbeads were degraded by DTT. The resulting product was directly used for mass spectrometry measurement.

Figure 12:
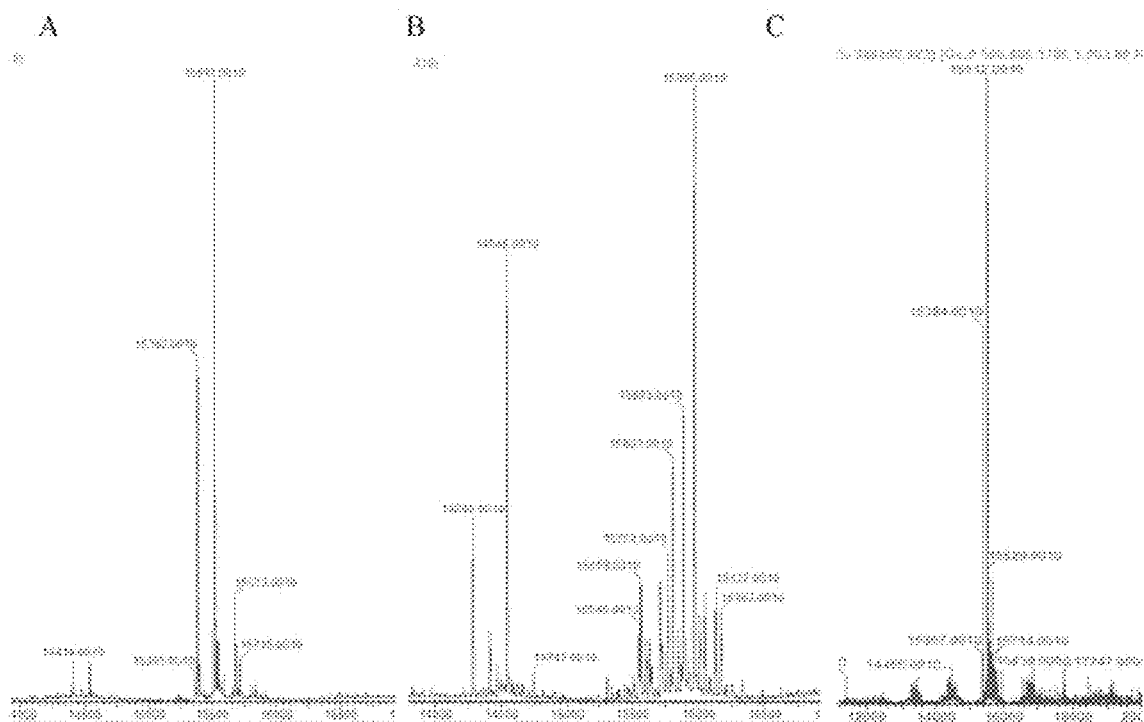
FIG. 12 shows a series of mass spectrometry results, which verifying that the degradable microbead according to the present invention can effectively capture the target protein which is then used for mass spectrometry measurement after the degradation of the microbead. The degradable microbead coupled with biotin according to the present invention captures the target protein from the cell culture lysate containing the target protein (avidin), then the microbead is treated by DTT, and the obtained protein sample is suitable for mass spectrometry measurement. Avidins from different sources (avidin-1 from corn and avidin-2 from egg) show different molecule weights in the mass spectrometry, corresponding to different glycosyl modifications.

SYNAPT G2-Si HDMS mass spectrometer from Waters equipped with a C18 reverse-phase chromatographic column was used, and the mobile phase was water:acetonitrile=99:1. By analysis with the official software of the mass spectrometer, the molecule weight spectrogram of the resulting sample was obtained (FIG. 12, the calculated molecule weight in Da as the horizontal axis). Among them, FIG. 12A shows the spectrogram of pure avidin-1, wherein the measured molecule weight for the main peak is 15511 Da. FIG. 12B shows the spectrogram of pure avidin-2, wherein two clusters of signals were measured, and the molecule weights of the main peaks are 14545 Da and 15965 Da, respectively. The molecular weights of the above pure products differ from 14343 Da—the theoretically calculated value of avidin protein sequence—by 1168 Da, 202 Da, and 1622 Da, respectively, presumably because avidins from different sources contain different glycosyl modifications. The mass spectrometry results of avidin-1 captured by the degradable microbeads (FIG. 12C) show that the molecule weight of the main peak is 15512, which is highly consistent with the result of pure avidin-1. It is demonstrated that the proteins obtained through the purification by using the degradable microbeads of the present invention are suitable for mass spectrometry measurement, and could differentiate different glycosyl modifications.

What is claimed is:

1. A degradable microbead comprising a polymer molecule crosslinked by a crosslinking agent, wherein the polymer molecule and/or the crosslinking agent comprises a sensitive chemical bond, wherein the sensitive chemical bond is cleavable through a chemical and/or light treatment, thereby resulting in the degradation of the degradable microbead, wherein
    (i) the polymer molecule is selected from the group consisting of polyacrylic acid-based compounds, polyacrylate-based compounds, polyacrylamide-based compounds, polyvinyl alcohol-based compounds, and polyethylene glycol-based compounds, and the crosslinking agent is selected from o-nitrophenylethyl alcohol-based compounds or o-nitrobenzyl alcohol-based compounds, wherein the sensitive chemical bond is provided by o-nitrophenylethyl alcohol-based compounds or o-nitrobenzyl alcohol-based compounds; or
    (ii) the polymer molecule is a copolymer of acrylamide and cystamine acrylamide, and the crosslinking agent is cystamine bisacrylamide, wherein the sensitive chemical bond is provided by cystamine-based compounds.

2. The degradable microbead according to claim 1, wherein the polymer molecule is selected from the group consisting of polyacrylic acid-based compounds, polyacrylate-based compounds, polyacrylamide-based compounds, polyvinyl alcohol-based compounds, and polyethylene glycol-based compounds; and the crosslinking agent is selected from o-nitrophenylethyl alcohol-based compounds or o-nitrobenzyl alcohol-based compounds, wherein the sensitive chemical bond is provided by o-nitrophenylethyl alcohol-based compounds or o-nitrobenzyl alcohol-based compounds.

3. The degradable microbead according to claim 1, wherein the polymer molecule is a copolymer of acrylamide and cystamine acrylamide, and the crosslinking agent is cystamine bisacrylamide, wherein the sensitive chemical bond is provided by cystamine-based compounds.

4. The degradable microbead according to claim 3, when prepared by reacting in water-in-oil reaction droplets, wherein the aqueous phase comprises acrylamide, cystamine bisacrylamide, cystamine acrylamide, and ammonium persulfate.

5. The degradable microbead according to claim 4, wherein the aqueous phase comprises by weight 6% acrylamide, 0.2% cystamine bisacrylamide, 0.5% ammonium persulfate, and 75 mM cystamine acrylamide.

6. The degradable microbead according to claim 1, having a diameter of 1 μm to 100 μm.

7. A method of separating a target protein from a sample comprising the target protein, comprising the steps of:
    1) Attaching an affinity ligand of the target protein to the degradable microbead according to claim 1;
    2) Contacting the sample with the degradable microbead, such that the target protein is attached to the degradable microbead through the affinity ligand;
    3) Separating the degradable microbead from the sample; and
    4) Degrading the degradable microbead by a chemical and/or light treatment to obtain the target protein.

8. The method according to claim 7, wherein the step 1) is performed by attaching the affinity ligand to the amino group on the cystamine acrylamide of the degradable microbead by the coupling agent glutaraldehyde.

9. The method according to claim 7, wherein the degradable microbead has a diameter of 1 μm to 100 μm.

10. The method according to claim 7, wherein the target protein is Flag-tagged, and the affinity ligand is an anti-Flag antibody; or the target protein is Strep-tagged, and the affinity ligand is a Streptactin protein.

11. The method according to claim 7, wherein the step 3) is performed by chromatography or centrifugation.

12. A method of observing a target protein by electron microscope, comprising separating the target protein by the method according to claim 7, and observing the target protein and analyzing the structure of the target protein by electron microscope.

13. A method of analyzing a target protein by mass spectrometry, comprising separating the target protein by the method according to claim 7, and analyzing the target protein by mass spectrometer.

14. The method according to claim 13, wherein the analyzing comprises detecting the molecule weight, mutation, post-translational modification, or polymerization status of the target protein.

15. The method according to claim 14, wherein the post-translational modification is acylation modification, alkylation modification, biotinylation modification, terpene-like modification, glycosylation modification, phosphorylation modification, esterification modification, nitrosation modification, ubiquitination modification, small ubiquitin-related modifier (SUMO) modification (SUMOylation), amination modification, hydroxylation modification, or carboxylation modification.

16. A method of qualitatively or quantitatively detecting a target protein in a sample, comprising a step of separating the target protein from the sample by the method according to claim 7.

* * * * *